US008920468B2

(12) United States Patent
Triplett et al.

(10) Patent No.: US 8,920,468 B2
(45) Date of Patent: Dec. 30, 2014

(54) POLYAXIAL ORTHOPEDIC FASTENEING APPARATUS WITH INDEPENDENT LOCKING MODES

(75) Inventors: Daniel J. Triplett, Providence, UT (US); Joel R. Helgerson, Providence, UT (US); Robert W. Hoy, Columbia, OH (US)

(73) Assignee: GMEDelaware 2 LLC, Audubon, PA (US)

( * ) Notice: Subject to any disclaimer, the term of this patent is extended or adjusted under 35 U.S.C. 154(b) by 502 days.

(21) Appl. No.: 13/270,599

(22) Filed: Oct. 11, 2011

(65) Prior Publication Data

US 2012/0029573 A1 Feb. 2, 2012

Related U.S. Application Data

(63) Continuation of application No. 11/312,323, filed on Dec. 19, 2005, now Pat. No. 8,062,336, which is a continuation-in-part of application No. 11/063,941, filed on Feb. 22, 2005, now Pat. No. 7,993,373.

(51) Int. Cl.
*A61B 17/70* (2006.01)
*A61F 2/44* (2006.01)
*A61F 2/30* (2006.01)
*A61F 2/46* (2006.01)

(52) U.S. Cl.
CPC ....... *A61F 2/4405* (2013.01); *A61F 2002/3085* (2013.01); *A61F 2002/30444* (2013.01); *A61B 17/70* (2013.01); *A61F 2002/30485* (2013.01); *A61F 2002/30016* (2013.01); *A61F 2002/30405* (2013.01); *A61F 2002/30538* (2013.01); *A61F 2220/0025* (2013.01); *A61F 2220/0041* (2013.01); *A61F 2002/30512* (2013.01); *A61F 2250/0019* (2013.01); *A61F 2250/0006* (2013.01); *A61B 17/7064* (2013.01); *A61F 2002/4677* (2013.01)
USPC ........... 606/247; 606/266; 606/279; 606/306; 606/308; 606/310

(58) Field of Classification Search
CPC ...... A61B 17/84; A61B 17/844; A61B 17/86; A61B 17/8605; A61B 17/861; A61B 17/7001; A61B 17/7064; A61B 17/7035; A61B 17/7038
USPC .......... 606/266–270, 287, 300–321, 326–328
See application file for complete search history.

(56) References Cited

U.S. PATENT DOCUMENTS

| 5,047,029 | A | * | 9/1991 | Aebi et al. | 606/264 |
| 5,474,551 | A | * | 12/1995 | Finn et al. | 606/264 |
| 5,501,684 | A | * | 3/1996 | Schlapfer et al. | 606/301 |
| 5,733,285 | A | * | 3/1998 | Errico et al. | 606/278 |
| 5,735,851 | A | * | 4/1998 | Errico et al. | 606/266 |

(Continued)

*Primary Examiner* — Jerry Cumberledge

(57) ABSTRACT

An apparatus is designed to attach an implant to bone in a manner that permits rotational adjustment of the implant about multiple axes prior to securement via the apparatus. The apparatus includes separate rotational and translational fasteners that can be individually locked to independently restrict rotation and translation of the implant relative to the bone. The rotational fastener includes an interpositional member, an expandable engagement member, and a rotational locking member that urges the expandable engagement member to advance along the interpositional member. The resulting expansion of the engagement member causes it to engage the implant. The rotational fastener is slidable along a fixation member implanted in the bone until the translational fastener is applied to restrict relative translation between the rotational fastener and the bone.

18 Claims, 3 Drawing Sheets

(56) References Cited

U.S. PATENT DOCUMENTS

| | | | | |
|---|---|---|---|---|
| 6,146,383 | A * | 11/2000 | Studer et al. | 606/308 |
| 6,187,005 | B1 * | 2/2001 | Brace et al. | 606/264 |
| 6,579,319 | B2 * | 6/2003 | Goble et al. | 623/17.11 |
| 7,445,635 | B2 * | 11/2008 | Fallin et al. | 623/17.11 |
| 7,588,590 | B2 * | 9/2009 | Chervitz et al. | 606/247 |
| 7,608,104 | B2 * | 10/2009 | Yuan et al. | 623/17.11 |
| 7,674,293 | B2 * | 3/2010 | Kuiper et al. | 623/17.11 |
| 2003/0028250 | A1 * | 2/2003 | Reiley et al. | 623/17.11 |
| 2003/0125741 | A1 * | 7/2003 | Biedermann et al. | 606/61 |
| 2004/0172022 | A1 * | 9/2004 | Landry et al. | 606/61 |
| 2005/0070901 | A1 * | 3/2005 | David | 606/61 |
| 2005/0131406 | A1 * | 6/2005 | Reiley et al. | 606/61 |
| 2005/0277931 | A1 * | 12/2005 | Sweeney et al. | 606/61 |
| 2006/0282074 | A1 * | 12/2006 | Renaud et al. | 606/61 |
| 2008/0009867 | A1 * | 1/2008 | Banouskou et al. | 606/61 |

* cited by examiner

POLYAXIAL ORTHOPEDIC FASTENEING APPARATUS WITH INDEPENDENT LOCKING MODES

CROSS REFERENCE TO RELATED APPLICATIONS

This patent application is a continuation application claiming priority to U.S. patent application Ser. No. 11/312,323, filed on Dec. 19, 2005 now U.S. Pat. No. 8,062,336, which is a continuation-in-part of U.S. patent application Ser. No. 11/063,941, filed on Feb. 22, 2005 now U.S. Pat. No. 7,993,373, the entire contents of which are incorporated by reference.

BACKGROUND OF THE INVENTION

1. The Field of the Invention

The present invention relates generally to systems and methods for attaching implants to bone, and more specifically, to a polyaxial orthopedic fastening apparatus particularly useful in the field of facet joint replacement.

2. The Relevant Technology

Orthopedic medicine provides a wide array of implants that can be attached to bone to alleviate various pathologies. One unique challenge in orthopedics is to provide implants and fastening devices that are adaptable to a variety of bone morphologies. Each patient will have a different bone structure; accordingly, it may be necessary to allow for adjustable positioning of an implant with respect to the bone so that the implant will be positioned to perform its function.

For this reason, a number of fixation systems have been invented that enable variation of the angle between the implant and the fastener. Although such fixation systems generally permit adaptation to the bone morphology of a patient to provide secure anchoring of the implant to bone, they are generally somewhat limited in the types of adjustment they permit with respect to the bone. Accordingly, such fixation systems may not be usable with a number of implants that require more comprehensive adjustability. Furthermore, many known implant fixation systems are complex due to the presence of several parts, or due to the need to perform several steps to utilize them to attach an implant to bone. Yet further, some known implant fixation systems are expensive, and require the use of unusual tooling. A need exists in the art for implant fixation systems and methods that alleviate the foregoing shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to anchor orthopedic implants to bone in a manner that provides a high degree of implant adjustability, simplicity, and ease of use. The present invention can be used in any orthopedic procedure, but may have particular utility in the field of facet joint replacement to alleviate back pain resulting from traumatic, inflammatory, metabolic, synovial, neoplastic and degenerative spinal disorders. The configuration and operation of selected embodiments of the invention will be shown and described in greater detail with reference to FIGS. 1 through 4, as follows.

In this application, the terms "fastener," "interpositional member," and "engagement member" are used broadly. A "fastener" generally relates to one or more members that can be used to "lock" two other objects together by restricting relative rotation and/or translation about or along at least one axis. More precisely, a "rotational fastener" is a fastener that restricts relative rotation of the two objects. A "translational" fastener is a fastener that restricts relative translation of the two objects. An "interpositional member" generally is a member, at least part of which is designed to be positioned between at least two other members of a system. An "engagement member" is a member that is movable into and/or out of contact with another member to accomplish a function such as locking the members together.

"Polyaxial" rotation is rotation that can occur about at least two axes that are not parallel to each other. "Triaxial rotation" is rotation about three perpendicular axes. Triaxial rotation is equivalent to rotation about a point, because free rotation about any axis of a 3D coordinate system is the same as rotation that is not limited to any axis in the system.

Figure 1:
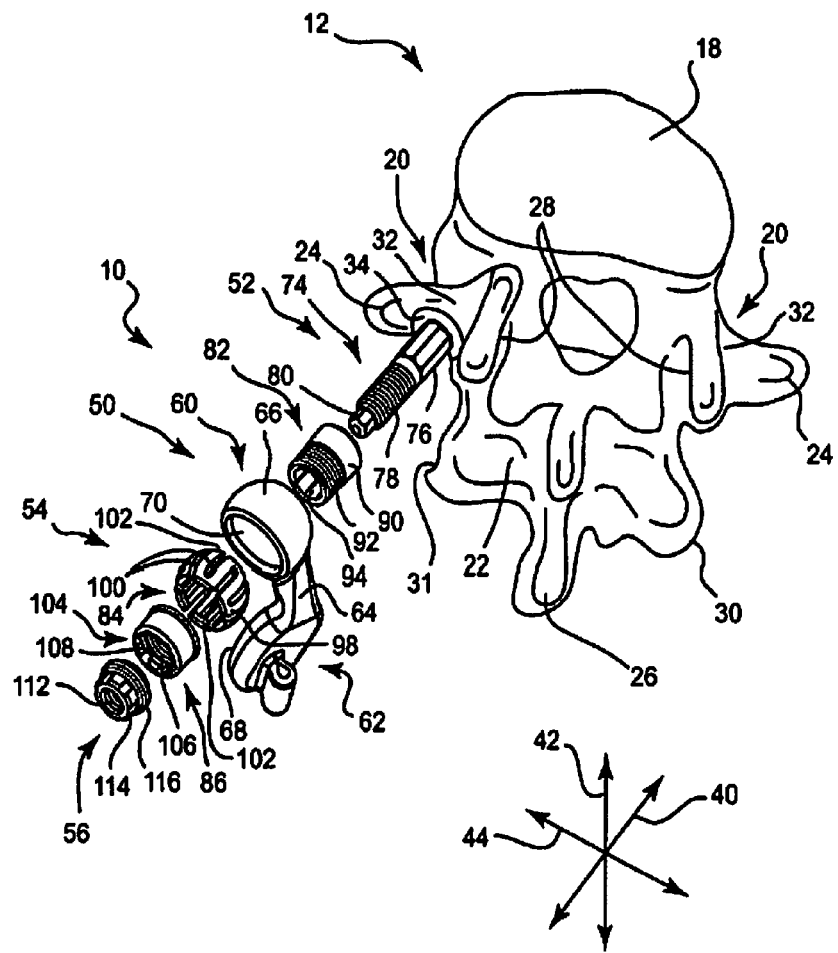
FIG. 1 is an exploded, perspective view of a vertebra with an apparatus according to one embodiment of the invention, with the apparatus positioned to attach an implant to the vertebra.

Referring to FIG. 1, a perspective view illustrates an apparatus 10 according to one embodiment of the invention, in use with a vertebra 12, such as an L 4 lumbar vertebra of a human spine. As shown, the vertebra 12 has a body 18, which is generally disc-shaped. The vertebra 12 also has two pedicles 20 extending from the body 18, and a posterior arch, or lamina 22, which extends between the posterior ends of the pedicles 20 to couple the pedicles 20 together. The vertebra 12 also has a pair of transverse processes 24 that extend laterally from the pedicles 20, and a spinous process 26 that extends posteriorly from the lamina 22.

The vertebra 12 also has a pair of superior facets 28, which are positioned toward the top of the vertebra 12 and face generally medially. Additionally, the vertebra 12 has an inferior facet 30, which is positioned toward the bottom of the vertebra 12 and faces generally laterally. A resected inferior facet 31 also faces generally laterally. The articular surface of the resected inferior facet 31 may optionally have been resected away to prepare the resected inferior facet 31 for arthroplasty. Each of the pedicles 20 of the vertebra 12 has a saddle point 32, which is positioned generally at the center of the juncture of each superior facet 28 with the adjacent transverse process 24.

The superior facets 28 of the vertebra 12 articulate (i.e., slide and/or press) against the inferior facets (not shown) of an adjacent superior vertebra (not shown), such as an L 3 lumbar vertebra, to limit relative motion between the vertebra 12 and the superior vertebra. Thus, the combination of each superior facet 28 with the adjacent inferior facet defines a facet joint (not shown). Accordingly, two facet joints span the distance between each adjacent pair of vertebrae. The inferior facets 30 of the vertebra 30 are part of other facet joints that control motion between the vertebra 12 and an adjacent inferior vertebra (not shown), such as an L 5 lumbar vertebra or the sacrum.

Each of the facet joints may be covered by a capsule (not shown) containing a fluid (not shown) that reduces wear of the facets 28, 30 and facilitates articulation. Additionally, layers of cartilage (not shown) may cover the facets 28, 30 to further reduce wear and facilitate articulation. These anatomical structures, as well as the various muscles, ligaments, and nerves of the spine, will not be depicted in the Figures to enhance the clarity of the disclosure. Such structures may be removed or displaced according to known methods to provide the necessary access to the vertebra 12.

As shown, a semispherical resection 34 has been formed on one of the saddle points 32 of the vertebra 12. The semispherical resection 34 is shaped to receive an implant to replace the articular surface of one or both of the adjacent superior and inferior facets 28, 30. The semispherical resection 34 permits relative rotation between the implant and the vertebra 12 about three perpendicular axes prior to fixation of the implant to the vertebra 12. The axes may be defined as shown by reference numerals 40, 42, and 44 in FIG. 1.

More precisely, the axes may include a first axis 40, a second axis 42, and a third axis 44. The first axis 40 is generally collinear with the axis of the corresponding pedicle 20. The second axis 42 is generally vertical (i.e., parallel to the axis of the body 18) and perpendicular to the first axis 40. The third axis 44 is generally horizontal (i.e., parallel to the end plates of the body 18) and perpendicular to the first and second axes 40, 42.

The apparatus 10 includes an implant 50, a fixation member 52, a rotational fastener 54, and a translational fastener 56. The implant 50 is designed to seat against the semispherical resection 34 and to replace the removed articular surface of the resected inferior facet 31 immediately inferior to it. The fixation member 52 may take the form of a pedicle screw designed to be implanted in the corresponding pedicle 20 to anchor the implant 50 in place. The orthopedic fastener 54 is designed to be coupled to the fixation member 52 to hold the implant against the vertebra 12.

In the embodiment of FIG. 1, the implant 50 has a fixation portion 60, an articulation portion 62, and a stem 64. The fixation portion 60 is shaped to be attached to the semispherical resection 34, and the articulation portion 62 provides a surface that articulates with an adjacent vertebral facet to carry out the function of the inferior facet 30. The articulation portion 62 is coupled to the fixation portion 60 by the stem 64.

As shown, the fixation portion 60 has a bone apposition surface 66, which may be generally semispherical to correspond to the shape of the semispherical resection 34. The fixation portion 60 also has an aperture (not visible in FIG. 1) that passes through the bone apposition surface 66 to receive the fixation member 52. The aperture is somewhat larger than the exterior surface of the fixation member 52 so that the bone apposition surface 66 is able to slide against the semispherical resection 34 with the fixation member 52 in place, implanted in the pedicle 20.

The articulation portion 62 similarly has an articulation surface 68 designed to articulate with a superior facet of a vertebra (or sacrum) immediately inferior to the vertebra 12. The articulation surface 68 may have a convex shape, which may further be semispherical, semicylindrical, or the like. The articulation surface 68 may be designed to articulate with a natural superior facet and/or a prosthetic superior facet.

In addition to the bone apposition surface 66, the fixation portion 60 also has an engagement surface 70 shaped to receive the rotational fastener 54 such that the rotational fastener 54 is able to restrict relative rotation between the implant 50 and the fixation member 52. The engagement surface 70 has a generally semispherical concave shape through which the aperture (not shown) of the fixation portion 60 passes.

In the embodiment of FIG. 1, the fixation member 52 has a distal end (not visible in FIG. 1) 74 implanted into the corresponding pedicle 20 of the vertebra 12, and a proximal end 74 that protrudes from the corresponding saddle point 32. The distal end has threads that facilitate implantation of the distal end 74 in the pedicle 20 and keep the implanted distal end in place. The fixation member 52 also has a sliding interface 76 positioned between the distal end and the proximal end 76. The sliding interface 76 may have a polygonal or other non-circular cross section shaped to receive the rotational fastener 54 in such a manner that no significant relative rotation can occur between the sliding interface 76 and the rotational fastener 54.

The proximal end 74 has a plurality of threads 78 that are exposed to receive the fastener 54. Additionally, the proximal end 74 has a torquing interface 80 that may be used to apply torque to the fixation member 52 to implant the distal end in the pedicle 20. The torquing interface 80 may take the form of a hexagonal recess or projection that mates with a corresponding hexagonal feature on a driver (not shown).

As shown, the rotational fastener 54 includes an interpositional member 82, an engagement member 84, and a rotational locking member 86. The interpositional member 82 may have a generally tubular shape with a tapered portion 90, a plurality of threads 92 adjacent to the tapered portion 90, and an interface 94. As shown, the tapered portion 90 becomes narrower toward the threads 92. The interface 94 is designed to provide a slidable, yet non-rotating connection between the interpositional member 82 and the sliding interface 76 of the fixation member 52. Accordingly, the interface 94 may take the form of a bore with a polygonal cross section that receives the corresponding polygonal cross section of the sliding interface 76 with enough clearance to permit relatively free sliding motion. Alternatively, a tighter fit may be used to restrict sliding, but permit relative translation between the interpositional member 82 and the fixation member 52 under the application of force.

As also illustrated in FIG. 1, the engagement member 84 is generally spherical in shape, with a hollow interior. The hollow interior has a taper that generally matches the taper of the tapered portion 90 of the interpositional member 82. The engagement member 84 has an implant engagement surface 98 with a semispherical shape, and a plurality of grooves 100 arranged in a parallel, substantially radially symmetrical fashion about the implant engagement surface 98. The grooves 98 permit expansion and contraction of the implant engagement surface 98. The hollow interior is accessible via ports 102 positioned at either end of the implant engagement surface 98.

The rotational locking member 86 has a bore 104 in which a plurality of threads 106 are formed. The threads 106 are designed to mate with the threads 92 of the interpositional member 82. The bore 104 also has a torquing interface 108 formed therein to facilitate rotation of the rotational locking member 86 into engagement with the interpositional member 82. The torquing interface 108 may take the form of a portion of the bore 104 having a generally polygonal cross sectional shape, such as a hexagonal cross sectional shape. Thus, a corresponding hexagonal protrusion of a driver (not shown) may be inserted into the torquing interface 108 to rotate the rotational locking member 86 into engagement with the interpositional member 82.

The translational fastener 56, which may also be termed a translational locking member, has a threaded bore 112, a torquing interface 114, and a flange 116. The threads of the threaded bore 112 are sized to rotate into engagement with the threads 78 of the proximal end 74 of the fixation member 52.

The torquing interface 114 may take the form of a protrusion having a generally hexagonal shape capable of being received within a recess of a driver (not shown) having a corresponding hexagonal shape.

The flange 116 protrudes generally radially from the exterior of the translational fastener 56, adjacent to the torquing interface 114. The flange 116 may be sized to abut the adjoining annular surface of the rotational locking member 86 to enable the translational fastener 56 to exert relatively uniform, linear force against the rotational locking member 86 upon tightening of the translational fastener 56. If desired, a portion of the translational fastener 56 may nest within the bore 104 of the rotational locking member 86 to reduce the profile of the assembled apparatus 10.

The apparatus 10 may be secured to the vertebra 12 according to a variety of methods. According to one method, the fixation member 52 is first implanted in the corresponding pedicle 20. This may be carried by, for example, forming an incision in the overlying tissues, retracting the tissues from the operating area, implanting a guide wire in the pedicle 20 under fluoroscopy, and then rotating the fixation member 52 into engagement with the pedicle 20 through the use of a driver (not shown) coupled to the torquing interface 80.

Through the use of the rotational fastener 54 and the translational fastener 56, the orientation of the implant 50 and the position of the implant 50 along the fixation member 52 (i.e., along the first axis 40) may be independently locked. The rotational fastener 54 and the implant 50 may first be assembled together by assembling the interpositional member 82, the engagement member 84, the rotational locking member 86, and the implant 50.

The engagement member 84 may first be inserted into the hollow interior of the fixation portion 60 of the implant 50. Since the engagement member 84 has not yet been significantly expanded, there is clearance between the implant engagement surface 98 of the engagement member 84 and the engagement surface 70 of the fixation portion 60 of the implant 50. This clearance permits rotation of the engagement member 84 within the fixation portion 60. The engagement surface 70 of the fixation portion 60 may have a semispherical shape that extends far enough to effectively capture the engagement member 84. Accordingly, the engagement member 84 may need to be compacted and/or pressed into the hollow interior of the fixation portion 60.

The interpositional member 82 is then inserted through the aperture (not shown) of the fixation portion 60 and into the hollow interior of the engagement member 84 such that the tapered portion 90 extends through the port 102 that will be oriented toward the fixation member 52, and the threads 92 extend through the other port 102 (i.e., the port 102 that will be oriented toward the translational fastener 56 and the rotational locking member 86, as shown in the exploded view of FIG. 1). Then, the rotational locking member 86 is positioned adjacent to the corresponding port 102 such that the threads 92 enter the bore 104.

The rotational locking member 86 is rotated with respect to the interpositional member 82 such that the threads 106 of the bore 104 engage the threads 92 of the interpositional member 82. Continued rotation of the rotational locking member 86 with respect to the interpositional member 82 will cause the engagement member 84 to expand as the opposite port 102 slides toward the larger end of the tapered portion 90. However, at this stage, the rotational fastener 54 remains in the unlocked configuration because the rotational locking member 86 is only rotated sufficiently to engage the threads 92 to keep the rotational locking member 86, the interpositional member 82, and the engagement member 84 together.

The assembled implant 50 and rotational fastener 54 may then be advanced toward the proximal end 74 of the implanted fixation member 52 such that the torquing interface 80, and then at least some of the threads 78, pass through the interface 94, or bore, of the interpositional member 82. The interface 94 then slides around the sliding interface 76 of the proximal end 74 of the fixation member 52. As mentioned before, some clearance may exist between the sliding interface 76 of the proximal end 74 and the interface 94 of the interpositional member 82. However, the matching polygonal shapes of the sliding interface 76 and the interface 94 prevent relative rotation between the fixation member 52 and the rotational fastener 54.

Since the rotational fastener 54 is still in the unlocked configuration, the implant 50 may be rotated with respect to the fixation member 52 and the vertebra 12. The implant 50 is pivoted generally about the center of the radius of the engagement surface 70 until the articulation surface 68 is properly positioned and oriented to articulate with the corresponding natural or prosthetic superior articulation surface. In the embodiment of FIG. 1, rotation of the implant 50 is not only polyaxial, but also triaxial. Thus, the implant 50 may be rotated about any axis passing through the center of the radius of the engagement surface 70.

Once the implant 50 has been rotated into the proper orientation with respect to the vertebra 12, it may be locked in that orientation by moving the rotational fastener 54 to the locked configuration. The rotational locking member 86 is further rotated with respect to the interpositional member 82, for example, by engaging the torquing interface 108 of the bore 104 with a corresponding feature of a driver (not shown). This rotation urges the opposite port 102 to advance along the tapered portion 90 of the interpositional member 82, toward the larger end of the tapered portion 90. The outward pressure on the port 102 causes the engagement member 84 to expand, thereby increasing the overall radius of the implant engagement surface 98. The implant engagement surface 98 engages the engagement surface 70 of the fixation portion 60 of the implant and exerts outward pressure on the engagement surface 70. As a result, the implant 50 becomes locked to the engagement member 84.

Thus, the rotational fastener 54 has reached the locked configuration, and the implant 50 is no longer rotatable with respect to the vertebra 12. However, the implant 50, together with the rotational fastener 54 that is now rigidly locked to it, may still move along the fixation member 52. The translational fastener 56 may then be applied to restrict such translational motion. More precisely, the translational fastener 56 is moved toward the proximal end 74 of the fixation member 52 such that the threads 78 of the proximal end 74 enter the threaded bore 112 of the translational fastener 56. The translational fastener 56 is rotated to advance the threaded bore 112 along the threads 78 until the flange 116 presses snugly against the adjoining annular surface of the rotational locking member 86. This effectively presses the bone apposition surface 66 of the fixation portion 60 of the implant 50 against the semispherical resection 34 of the corresponding saddle point 32.

Figure 2:
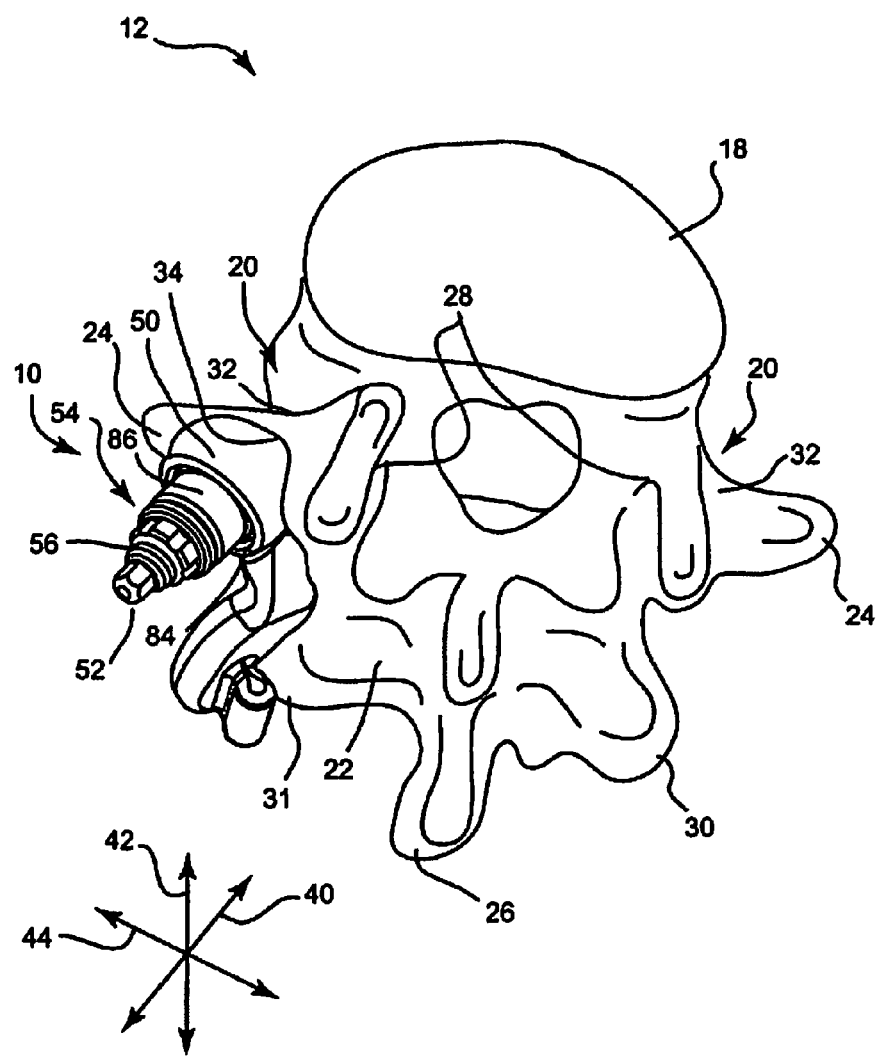
FIG. 2 is a perspective view of the vertebra with the apparatus of FIG. 1 secured to the vertebra in the locked configuration to lock both rotation and translation of the implant.

Referring to FIG. 2, a perspective view illustrates the apparatus 10 in fully assembled form on the vertebra 12. The position and orientation of the implant 50 are fixed with respect to the vertebra 12. Advantageously, since the orientation and position of the implant 50 are independently locked, any subsidence of the bone around the saddle point 32 will not enable the implant 50 to rotate from its desired orientation with respect to the vertebra 12. If such subsidence occurs, the position of the implant 50 may be stabilized with relatively simple revision surgery, i.e., by further tightening the translational fastener 56 or by inserting bone graft, an implant, or some other form of support into the space between the bone apposition surface 66 and the semispherical resection 34.

Those of skill in the art will recognize that an apparatus similar to the apparatus 10 may be applied to the opposite side of the vertebra 12 for bilateral operation. The fixation member 52, rotational fastener 54, and translational fastener 56 may be used to attach left or right, superior and/or inferior, implants to the vertebra 12. In alternative embodiments (not shown), similar components to the components 52, 54, and 56 may even be used to secure nested fixation portions of superior and inferior implants to a single saddle point 32. In yet other alternative embodiments, such similar components may be used to secure other types of implants to the vertebra 12 besides facet joint implants, including but not limited to artificial discs, posterior rod fixation systems, dynamic stabilization systems, and the like (not shown).

Figure 3:
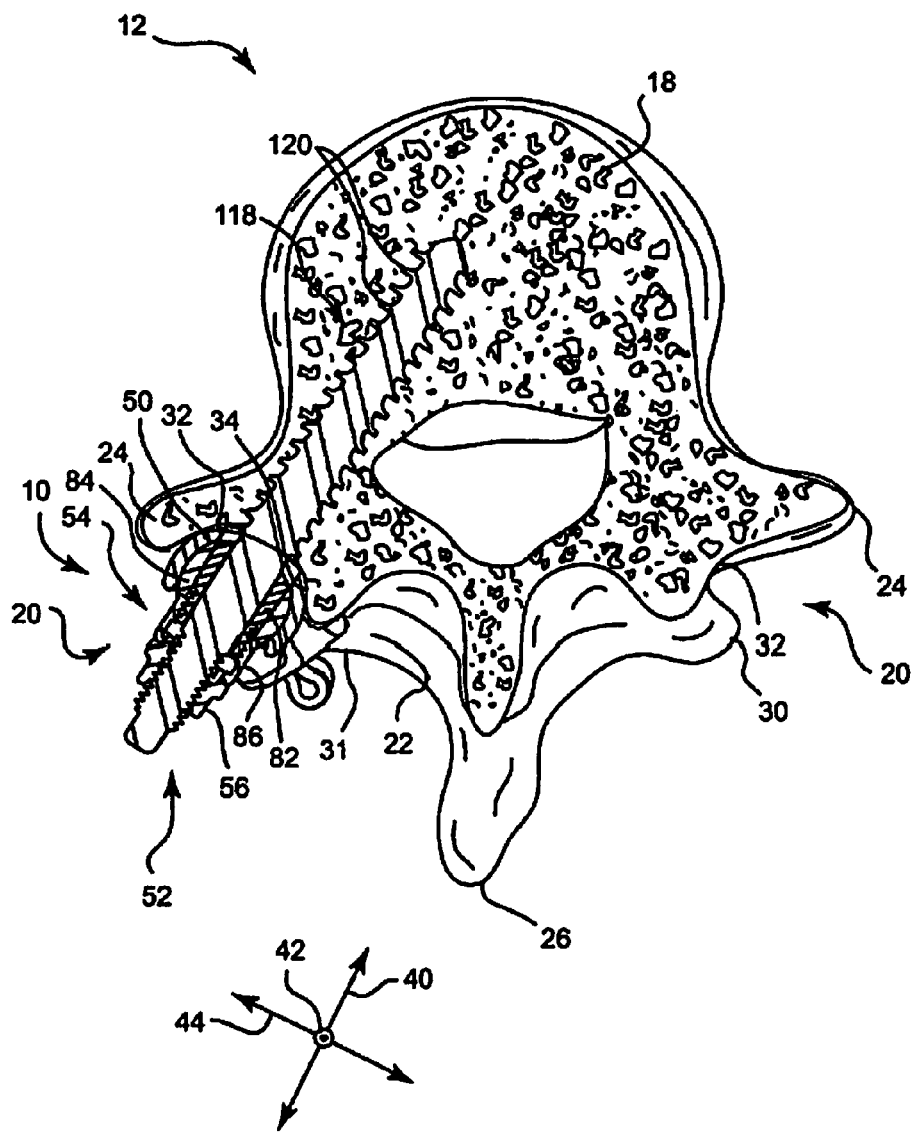
FIG. 3 is a cephalad, section view of the vertebra with the apparatus of FIG. 1 secured to the vertebra in the locked configuration as in FIG. 2.

Referring to FIG. 3, a cephalad, section view illustrates the apparatus 10 in fully assembled form on the vertebra 12. As mentioned previously, the fixation member 52 has a distal end 118 with threads 120 that engage the interior of the corresponding pedicle 20. Another potential advantage to independent rotational and translational locking of the implant 50 is that the purchase of the threads 120 within the pedicle 20 is not significantly challenged by any of the steps used to lock the orientation of the implant 50 with respect to the vertebra 12. Only the axial force exerted by locking of the translational fastener 56 is transmitted to the interface between the threads 120 and the surrounding bone. This decreases the probability that the bone between the threads 120 will fail under shear and permit the distal end 118 to pull free of the bone.

The present invention has particular relevance to orthopedic medicine, and more particularly to facet joint replacement. However, the principles, structures, and methods of the present invention may also be extended to a wide variety of other fields.

The present invention may be embodied in other specific forms without departing from its spirit or essential characteristics. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for securing an implant to a bone having independent rotational and translational locking through the use of an orthopedic fastener comprising an engagement member, an interpositional member, and a fixation member, the method comprising:
   sliding the implant translationally along the fixation member and against the bone to rotate the implant with respect to the bone about a first axis;
   urging the engagement member toward the bone along a direction nonparallel to the first axis;
   in response to urging the engagement member, moving the orthopedic fastener from an unlocked configuration in which the engagement member is rotatable with respect to the interpositional member, to a first locked configuration in which relative rotation between the interpositional member and the engagement member is restricted;
   in response to urging the engagement member toward the bone, urging the implant toward the bone;
   in response to motion of the orthopedic fastener to the first locked configuration, restricting relative rotation between the implant and the bone about the first axis; and
   applying a second locked configuration such that translational motion of the implant along the fixation member is restricted.

2. The method of claim 1, further comprising implanting the fixation member in the bone, the fixation member having a receiving interface, wherein urging the engagement member toward the bone comprises advancing the engagement member along the receiving interface.

3. The method of claim 1, wherein the bone comprises a vertebra, wherein sliding the implant against the bone comprises positioning an articular surface of the implant to replace a natural articular surface of a facet of the vertebra.

4. The method of claim 1, wherein moving the orthopedic fastener from the unlocked configuration to the first locked configuration comprises deforming at least one of the engagement member and the interpositional member to lock against the other of the engagement member and the interpositional member.

5. The method of claim 1, wherein the interpositional member comprises an implant interface having a generally conical shape.

6. The method of claim 1, further comprising:
   sliding the implant against the bone to rotate the implant with respect to the bone about a second axis perpendicular to the first axis; and
   in response to motion of the orthopedic fastener to the first locked configuration, restricting relative rotation between the implant and the bone about the second axis.

7. A method for securing an plant to bone having a rotational fastener comprising an interpositional member, an engagement member, and a rotational locking member, the method comprising:
   forming an incision in a vertebral body;
   implanting a fixation member through the incision;
   operably attaching the implant configured to replace a portion of a facet joint to the fixation member and sliding the implant translationally along the fixation member;
   rotating and pivoting the implant with respect to the fixation member until the implant is positioned and oriented to articulate as part of the facet joint;
   restricting rotational movement of the implant relative to the fixation member by rotating the rotational locking member and advancing the rotational locking member along the interpositional member to cause the engagement member to expand, thereby preventing any relative rotation between the implant and the fixation member, but allowing translational motion along the fixation member; and
   independently restricting translational movement of the implant relative to the fixation member.

8. The method of claim 7, wherein the incision is formed at a pedicle.

9. The method of claim 7, wherein the implant comprises a fixation portion, a stem and an articulation portion.

10. The method of claim 9, wherein the articulation portion provides a surface that articulates with an adjacent vertebral facet to carry out the function of an inferior facet.

11. The method of claim 9, wherein the fixation portion has a generally semispherical bone apposition surface.

12. The method of claim 9, wherein the fixation portion is configured to receive a translational fastener to restrict relative translational movement between the implant and the fixation member.

13. The method of claim 12, wherein the translational fastener includes a threaded bore configured to engage the fixation member, a torquing interface configured to engage a driver, and a flange configured to exert a linear force against the rotational locking member.

14. A method for securing an implant configured to replace a portion of a facet joint to bone having a rotational fastener comprising an interpositional member, and engagement member, and a rotational locking member, the method comprising:
   forming an incision in tissue overlying a pedicle;
   retracting the tissue;
   inserting a guidewire in the pedicle to serve as a guide for a fixation member;
   implanting the fixation member through the pedicle;
   operably attaching the implant to the fixation member and sliding the implant translationally along the fixation member;
   rotating and pivoting the implant with respect to the fixation member until the implant is positioned and oriented to articulate as part of the facet joint;
   restricting rotational movement of the implant relative to the fixation member by advancing the rotational locking member along the interpositional member to cause the engagement member to expand, thereby preventing any relative rotation between the implant and the fixation member, but allowing translational motion along the fixation member; and
   independently restricting translational movement of the implant relative to the fixation member.

15. The method of claim 14, wherein the implant comprises a fixation portion, a stem and an articulation portion.

16. The method of claim 15, wherein the articulation portion provides a surface that articulates with an adjacent vertebral facet to carry out the function of an inferior facet.

17. The method of claim 15, wherein the fixation portion has a generally semispherical bone apposition surface.

18. The method of claim 15, wherein the fixation portion is configured to receive a translational fastener to restrict relative translational movement between the implant and the fixation member.

* * * * *